US010321882B2

(12) United States Patent
Exelmans et al.

(10) Patent No.: US 10,321,882 B2
(45) Date of Patent: Jun. 18, 2019

(54) METHOD FOR CONTROLLING MULTIPLE WIRELESS SELF-TRIGGERING RADIOGRAPHIC IMAGE SENSORS IN A SINGLE EXPOSURE

(71) Applicant: AGFA NV, Mortsel (BE)

(72) Inventors: Walter Exelmans, Mortsel (BE); Eric De Broeck, Mortsel (BE)

(73) Assignee: AGFA NV, Mortsel (BE)

( * ) Notice: Subject to any disclaimer, the term of this patent is extended or adjusted under 35 U.S.C. 154(b) by 179 days.

(21) Appl. No.: 15/308,618

(22) PCT Filed: May 27, 2015

(86) PCT No.: PCT/EP2015/061633
§ 371 (c)(1),
(2) Date: Nov. 3, 2016

(87) PCT Pub. No.: WO2015/181196
PCT Pub. Date: Dec. 3, 2015

(65) Prior Publication Data
US 2017/0143286 A1    May 25, 2017

(30) Foreign Application Priority Data
May 27, 2014 (EP) .................... 14170081

(51) Int. Cl.
*A61B 6/00* (2006.01)
(52) U.S. Cl.
CPC .......... *A61B 6/4266* (2013.01); *A61B 6/4233* (2013.01); *A61B 6/5241* (2013.01); *A61B 6/54* (2013.01); *A61B 6/548* (2013.01)

(58) Field of Classification Search
CPC ....... A61B 6/4266; A61B 6/54; A61B 6/4233; A61B 6/5241; A61B 6/548
See application file for complete search history.

(56) References Cited

U.S. PATENT DOCUMENTS

| 5,887,049 A | 3/1999 | Fossum |
| 6,972,411 B2 | 12/2005 | Schick et al. |
| 7,436,444 B2 | 10/2008 | Endo |

(Continued)

FOREIGN PATENT DOCUMENTS

| EP | 0 919 858 A1 | 6/1999 |
| EP | 1 467 226 A1 | 10/2004 |

(Continued)

OTHER PUBLICATIONS

Official Communication issued in International Patent Application No. PCT/EP2015/061633, dated Sep. 10, 2015.

*Primary Examiner* — Chih-Cheng Kao
(74) *Attorney, Agent, or Firm* — Keating and Bennett, LLP (57) ABSTRACT

A method for triggering image capture by a group of simultaneously X-ray exposed multiple wirelessly inter-linked self-triggering direct radiography (DR) detector assemblies includes the steps of performing an initiation step to identify the group of participating DR detector assemblies prior to X-ray exposure, detecting the X-ray exposure by a first participating DR detector assembly, the first participating DR detector assembly performing a trigger step to signal all participating DR detector assemblies to start image capture.

9 Claims, 5 Drawing Sheets

(56) References Cited

U.S. PATENT DOCUMENTS

| | | | |
|---|---|---|---|
| 2004/0247081 A1* | 12/2004 | Halsmer | A61B 6/00 378/108 |
| 2011/0013746 A1* | 1/2011 | Zeller | A61B 6/145 378/98 |
| 2011/0064193 A1 | 3/2011 | Minnigh et al. | |
| 2012/0049080 A1* | 3/2012 | Enomoto | A61B 6/4233 250/371 |
| 2012/0051519 A1 | 3/2012 | Abe | |
| 2014/0086391 A1 | 3/2014 | Ohta et al. | |
| 2014/0103220 A1 | 4/2014 | Ohta et al. | |

FOREIGN PATENT DOCUMENTS

| | | |
|---|---|---|
| EP | 2 423 746 A1 | 2/2012 |
| EP | 2 543 318 A1 | 1/2013 |

\* cited by examiner

METHOD FOR CONTROLLING MULTIPLE WIRELESS SELF-TRIGGERING RADIOGRAPHIC IMAGE SENSORS IN A SINGLE EXPOSURE

CROSS REFERENCE TO RELATED APPLICATIONS

This application is a 371 National Stage Application of PCT/EP2015/061633, filed May 27, 2015. This application claims the benefit of European Application No. 14170081.5, filed May 27, 2014, which is incorporated by reference herein in its entirety.

BACKGROUND OF THE INVENTION

1. Field of the Invention

The present invention relates to a method for obtaining a composite image using direct digital radiographic imaging. More specifically the invention is related to direct digital radiography using multiple wireless digital sensors.

2. Description of the Related Art

In traditional analog radiography, used e.g. in medical applications, imaging is performed by means of a light sensitive photographic film in combination with a phosphor layer which converts the incident X-rays to visible light. The light emitted by the phosphor is captured by the film which is developed to obtain an image on the film. Typically, different sizes of assemblies which may be conceived as cassettes or as film packages are used in daily practice ranging from a few squared cm (for e.g. dental applications) up to e.g. 35 cm*43 cm for a relatively large field of view used in chest X-rays. The drawback of film based systems is that they require that the photographic film has to be chemically processed, leading to chemical waste products and loss of time.

More recently, digital X-ray systems, now known as computed radiography (CR) systems use a stored energy releasing phosphor sheet which is exposed to a radiation image during X-ray exposure. The stimulable phosphor stores the radiation image at exposure where after the stored energy image is read out using stimulating radiation scanning the phosphor plate, releasing the image-wise stored energy as light. The light is detected and an electronic image is generated by the light sensor and processing electronics, where after it is digitized.

Digital radiography (DR) is a form of X-ray imaging, where digital flat panel detectors, also called DR detectors, are used instead of traditional photographic film or cassette based CR systems. Advantages include time efficiency through bypassing chemical processing (compared to traditional film based systems) and through immediate read-out of the image data from the sensor (compared to cassette based CR systems where the read-out of the detector is done by means of a dedicated digitizer system).

The advantages of the DR detector and DR detector assembly design include compact size and immediate access to digital images. The performance of DR systems greatly exceeds the performance of CR systems, which have conversion efficiencies of 20-35%, and of screen-film systems for chest radiography, which have nominal conversion efficiencies of 25%. Also the ability to digitally enhance images are important advantages of digital systems. DR detectors or flat panel detectors exist in 2 different categories; indirect and direct flat panel sensors. A DR detector is the active electrical component capable of capturing the digital image, and is the most important subcomponent of a DR detector assembly or cassette. The DR detector assembly comprises also the cassette housing, a battery, the read-out electronics, a memory, and the modules which support the wireless or wired data communication with the modality workstation.

Direct flat panel detectors convert X-ray photons directly into an electric charge. The outer layer of this type of detector in this design is typically a high-voltage bias electrode. X-ray photons create electron-hole pairs in a-Se (amorphous Selenium), and the transit of these electrons and holes depends on the potential of the bias voltage charge. As the holes are replaced with electrons, the resultant charge pattern in the selenium layer is read out by a TFT array, active matrix array, electrometer probes or microplasma line addressing.

Indirect flat panel detectors combine an a-Si (amorphous Silicon) detector with a scintillator in the detectors outer layer. The scintillator typically consists of caesium iodide (CsI) or gadolinium oxysulfide ($Gd_2O_2S$) which transforms the incident X-rays into visible light. This visible light is channeled through the a-Si layer which converts it to a digital output signal by means of a TFT (thin film transistor) array.

A DR detector is generally packaged in a suitable format for the application in an assembly (a "DR detector assembly" or "image sensor"). This DR detector assembly comprises the DR detector itself and at least the electronics to read-out the digital image. The DR detector assembly is designed to meet the form and fit requirements of the intended application.

Commercial versions of the aforementioned DR detectors are nowadays available in different dimensions and pixel resolutions, depending on the targeted clinical imaging application (such as dental, general radiology, mammography . . . ). However the maximum size of the DR detector is mainly limited by the maximum size that commercial production processes can produce at an acceptable cost. The reality of today is that commercially available DR detectors do not exceed the maximum traditional X-ray sensor sizes as being used throughout the different technology transitions described here above. One of the largest field of view sizes used in X-ray chest imaging, a radiology application which typically requires the largest possible field of view, is currently 17×17 inch.

Certain clinical applications such as "full leg" or "full spine" radiography however require larger fields of view in order to cover the entire body part under examination, a problem which traditionally is overcome by combining and arranging different cassettes or DR detector assemblies in such way that a contiguous, larger field of view can be obtained. This has been described in detail in EP0919858.

Since DR detectors have the advantage that they can be read out directly at the position of acquisition, the use of DR detectors for this application have led to a number of new approaches on how to extend the field of view of a DR based system.

One solution to perform large field of view acquisitions, is for instance to use a single movable DR detector assembly which is moved in between the acquisitions of the subimages in order to reposition the DR detector assembly for the next subimage acquisition. The DR detector assembly moves from one to the next sub image position to complete the entire desired field of view range. This technique has been described in U.S. Pat. No. 7,265,355. The technique has the advantage that only one DR detector assembly needs to be used, but has the disadvantage that the contiguous image has to be acquired in a series of sub-exposures, which induces the risk that the patient moves between the acquisitions of the different subimages, since the time to acquire these images takes several seconds, resulting in an uncontiguous patient image.

A better solution to obtain large field of view images is to use multiple partially overlapping DR detector assemblies simultaneously during a single exposure. The use of different DR detector assemblies simultaneously has the advantage that the large field of view acquisition is shot in one single exposure, which ensures that there is no risk for patient movement during the single acquisition.

This overlapping technique has been described in combination with DR detector assemblies in the art in EP1467226, and comes along with a number of intrinsic challenges which need to be overcome in order to obtain an acceptable image result. The said referenced publication EP1467226 describes how the images from the different DR detector assemblies can be acquired and digitally processed after acquisition in order to end up with a single digital image whereby the geometries of the subimages are adjusted, and the overlapping areas showing the edges of the DR detector assemblies are removed from the resulting image.

A particular technical characteristic of any DR detector is that (as opposed to a CR sensor or conventional screen film techniques) an active signal needs to be sent to the DR detector (called "trigger") to signal it that the exposure will start. The trigger signal puts the DR detector in a state that it starts accumulating charges generated by the irradiation source, to build up the radiographic image. Also, the duration information of the exposure is sent to the DR detector to allow it to stop the image acquisition after a predetermined period of time. The reason to make sure that the acquisition time is limited to the exposure time only, is that in a DR detector, even in a state in which X-rays are not being irradiated, charges are generated due to dark current and alike, and these charges are accumulated in DR detector portions that detect the X-rays. Therefore, it is important to limit the acquisition time to the duration of the exposure. In most DR detectors, this acquisition state is preceded by an erase phase during which the unwanted accumulated charges causing background noise in the image are erased from the sensor, before it can be put in the acquisition phase.

Consequently, it is important that the DR detector is switched to its acquisition state as soon as the irradiation starts, and switches off when irradiation ends. In case the DR detector would be switched on too late, only a fraction of the irradiated dose would contribute to the radiographic image leading to a suboptimal image quality of the acquired image (or even worse, the acquisition would not detect any irradiation, and no image would be generated).

In a typical DR system, the DR detector is triggered to start the acquisition by means of an electrical signal running from the X-ray generator assembly to the DR detector. The duration of the acquisition is similarly communicated to the DR detector from the generator or X-ray system console.

Wireless DR detectors have become commercially available since 2009. Wireless DR detectors are DR detectors assemblies which can operate without being physically connected by a wire to a workstation. This type of DR detector assemblies are not integrated into a positioning device or a table, which means that they can be handled from a usability point-of-view in a similar way as CR detectors. With wireless DR detectors it is mandatory to use a wireless LAN for communications between the wireless DR detector and the workstation console. This way each performed radiograph is transferred at almost real time from the wireless DR detector to the workstation. The wireless DR detector assembly includes a built-in battery to supply power and this allows the sensor's necessary autonomy to obtain several radiographs and to transfer the obtained radiographs to the acquisition workstation for further viewing.

In wireless DR detectors, the trigger mechanism to start the acquisition needs to be generated within the wireless DR detector itself. This mechanism should pick up the early signs of an irradiation started at the X-ray source and hitting the wireless DR detector, and should trigger the wireless DR detector as soon as possible to start the acquisition state of the wireless DR detector. The many implementations described in the art mostly rely on mechanisms whereby a radiosensitive element in the wireless DR detector assembly detects incoming radiation, and will self-trigger the imaging sensor upon exceeding a measured radiation threshold value. U.S. Pat. Nos. 7,436,444 and 5,887,049 describe an implementation of such a self-triggering mechanism of a wireless DR detector whereby a dedicated radiosensitive element measures the incident exposure irradiation and will cause a driving circuit to generate the trigger as soon as a threshold value is exceeded.

US2014/0086391 describes a similar implementation of a self-trigger mechanism for a single wireless DR detector, but in this case multiple areas of the detector area of the DR detector are used to detect the incident irradiation. Different areas of the DR detector are used in order to have the area where the irradiation threshold is exceeded first trigger the entire sensor to start the image acquisition. This method allows for a higher probability to detect the start of the X-ray irradiation as soon as possible, and thus to self-trigger the wireless DR detector in time.

U.S. Pat. No. 6,972,411 describes another implementation of a self-trigger mechanism for a single detector in an intraoral application whereby the trigger signal is taken from a measurement of the total amount of current drawn from the entire detector. The entire area of the DR detector is used to monitor the start of the X-ray exposure.

US20140103220A1 discloses a triggering method applied within a DR detector assembly comprising 2 DR detectors, one which is intended for continuous fluoroscopic imaging, and the other to capture a higher resolution still image of the same patient area of interest, but at a higher resolution. The trigger method interrupts the fluoroscopic image capturing The aforementioned necessity to accurately activate the acquisition time window for the DR detector needs also to be considered when performing large field of view radiography using multiple wireless DR detectors in a single exposure. In this case, it is important that all wireless DR detectors used in the large field of view exposure are put in their active modes as soon as the X-ray irradiation starts. For that to happen, all involved wireless DR detectors need to be identified correctly and need to be signaled individually to start the acquisitions of the different participating wireless DR detectors.

The problem which arises under the circumstances described above is that when using multiple independent wireless DR detectors, these wireless DR detectors upon exposure will be self-triggered independently from each other, which may cause that some of the wireless DR detectors may self-trigger (too) late to capture the maximum of the exposed dose or—in the worst case—may not self-trigger at all. Each individual wireless DR detector will self-trigger to start its acquisition only when a predefined (dose) threshold value will have been exceeded in one or more radiosensitive areas in the DR detector assembly, depending on the self-trigger mechanism in place. The time delay which the self-triggering mechanism suffers after the exact moment of the exposure start for each individual wireless DR detector will mainly depend on the position of the radiosensitive area of the self-triggering mechanism for each wireless DR detector in the radiation field.

The position of the radiosensitive area in the irradiation beam will determine the dose rate which is captured by the radiosensitive areas of the self-triggering mechanism. The relative dose rate of a certain position compared to another position in the irradiation field is determined by many factors, such as: the characteristics of the X-ray source (for instance, the "heel"-effect of a typical rotating anode tube causes a dose gradient in the irradiation field), any object (the patient, parts of the sensor assembly, collimator) attenuating the X-ray beam, the relative distance from the X-ray source, the relative coverage of the DR detector surface by the X-ray beam, etc . . . .

These differences will cause the individual identical wireless DR detectors to be triggered at different moments in time, which may lead—as previously explained—to suboptimal image quality across the sub-images, or—even worse—a loss of image.

SUMMARY OF THE INVENTION

Preferred embodiments of the invention provide for a method for triggering image capture by a group of simultaneously X-ray exposed multiple wirelessly interlinked self-triggering direct radiography (DR) detector assemblies, and resolves above-mentioned aspects by the method as described below.

It provides for a method for triggering image capture by a group of simultaneously X-ray exposed multiple wirelessly interlinked self-triggering direct radiography (DR) detector assemblies, comprising the steps of performing an initiation step to identify said group of participating DR detector assemblies prior to X-ray exposure, detecting said X-ray exposure by a first participating DR detector assembly, said first participating DR detector assembly performing a trigger step to signal all participating DR detector assemblies to start image capture.

In the context of this invention, multiple wireless self-triggering DR detectors need to be understood as a set of at least 2 wireless self-triggering DR detector assemblies which are arranged in such way to form together a larger sensor imaging surface in comparison to the surface of a single DR detector. In a particular preferred embodiment used for "full leg/full spine" applications, the number of panels used simultaneously is typically 2, 3 or 4, but in principle there is no limitation to the number of used DR detectors. When applying this same technique on radiography in other diagnostic fields, the number of different DR detector assemblies used at the same time is unlimited, but is determined by the number of DR detector assembly surfaces needed to cover the area of interest to be imaged. It may be envisaged that up to 20 DR detectors may be required to image for instance a large animal entirely.

In a particular preferred embodiment used for "full leg/full spine" applications, the DR detector assemblies are organized in a particular way (namely, lined up on one axis) and the edges of the detectors will partially overlap each other. The application of the invention described here is however not limited to any specific ordering of the DR detectors, nor is it required that they are ordered in an overlapping way.

In this invention, a DR detector assembly (or "image sensor" or "cassettes") is a fully functional and packaged DR detector. The assembly includes at least the DR detector (or detection panel), a driving circuit and a housing (an example of a DR detector assembly is given in US 2014/0086391A1 [0052]-[0073] in more detail). The DR detector itself is the detection panel or the imaging pixel array intended to capture the radiographic image, and refers to the imaging sensor alone.

The triggering of the DR detector has to be understood as giving the signal that puts the DR detector in a state that it starts the acquisition phase. The acquisition phase is the period during which the DR detector is accumulating charges generated by the irradiation source, to build up the radiographic image. The triggering of a group of sensors relates to giving this trigger signal to the participating members of this group.

The wireless versions of DR detector assemblies are required to have a number of specific characteristics which separates them from non-wireless DR detector assemblies:

They need to have the capability to record in an autonomous way a radiographic image, and they need to be able to trigger themselves autonomously to start recording the radiographic exposure as soon as the X-ray source starts the exposure. They also need to be able to autonomously record and store the accumulated image from the time the image is acquired till it is transferred to the modality workstation for processing. Another required feature is that data communication with a processing workstation has to be performed wirelessly, which is why wireless DR detector assemblies need to be able to communicate wirelessly with other devices.

In the case of "wirelessly interlinked" DR detector assemblies, the assemblies or cassettes are capable of establishing a wireless data communication connection between the individual DR detector assemblies themselves. This wireless connection can rely on standard wireless networking techniques (Wifi), as well as their alternatives, such as bluetooth, visible or IR light, sound or ultrasound, or any other wireless communication method, and is in the context of this invention intended to send and/or receive the DR detector trigger signal, and other status information related to the DR detector assemblies.

The wireless DR detector assemblies are self-triggering, which means that each individual detector assembly is equipped with a mechanism to detect the start of the exposure (the exposure event), in order to trigger its own acquisition phase autonomously.

A single exposure may be a continuous intensity exposure during a certain exposure time or the radiation source (e.g. X-ray tube) can be used in another mode, e.g. exposure methods are known wherein the radiation source is varied in intensity or the x-ray tube is driven in a pulsed manner. These modes are usually combined with a sensor to detect the radiation dose already received and to regulate in real-time the exposure in view the density of the object to be examined. The meaning of single exposure in the context of this invention refers to the point that the different sub-images are acquired at the same moment in time, and thus that the different DR detectors are exposed simultaneously.

The participating DR detectors are those DR detectors which are located in the irradiation beam during the single exposure, and which will contribute in creating the composite large image. The participating DR detectors are identified during the initiation step.

When using multiple wireless DR detector assemblies during a single exposure, and leaving the start of the acquisition for each individual assembly up to its own self-triggering mechanism, it is in practice not possible to have all DR detectors start their recordings at the same time.

Due to the self-triggering mechanism which is foreseen in each individual assembly, the decision whether to start the recording depends on whether a threshold dose has been exceeded at the position of the individual DR detector assembly, and not at the optimal moment of the earliest detection of the start of the exposure by the best positioned detector assembly in the group. The new trigger-mechanism disclosed in this invention has the advantage that the image recording will start at the same time for all participating DR detector assemblies, and for some of the said detectors at an earlier moment in time compared to techniques or situations described in the art.

The results of this is that when a DR detector in the group of panels is triggered earlier due to this technique; less unused dose will be spoiled/lost which has an impact on improved image quality (and in extreme cases) on patient safety, since it can prevent the need for a retake in extreme conditions (when a detector would fail to self-trigger in time).

Further advantages and preferred embodiments of the present invention will become apparent from the following description and drawings.

Specific examples and preferred embodiments are set out below.

DETAILED DESCRIPTION OF THE PREFERRED EMBODIMENTS

In the following detailed description, reference is made in sufficient detail to the above referenced drawings, allowing those skilled in the art to practice the preferred embodiments explained below.

Figure 1:
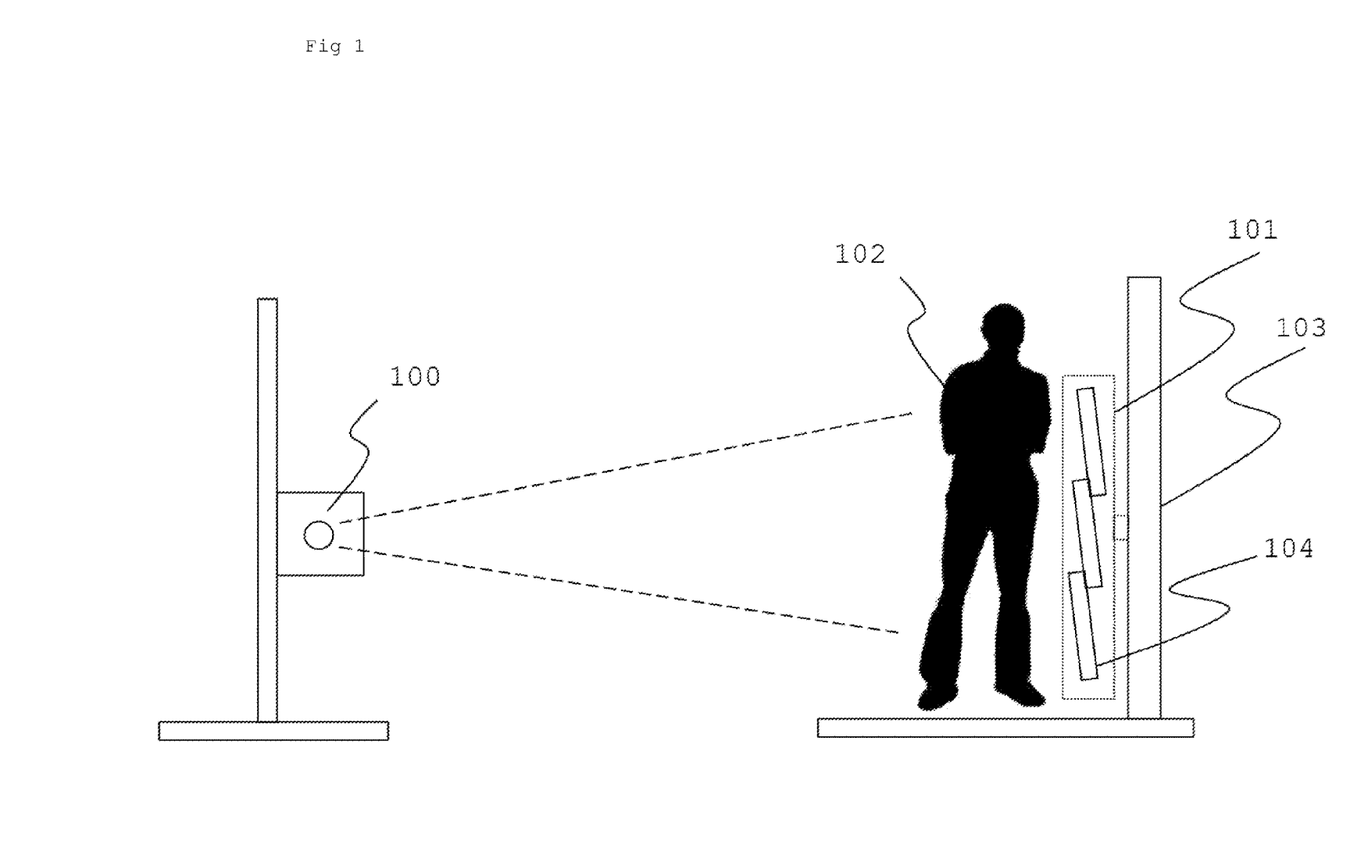
FIG. 1 shows an example of a setup of an X-ray system intended for large field of view radiography.

In FIG. 1, [100] represents the X-ray source, [102] the patient, and a detector or cassette holder [101] attached to a floor stand [103] holding multiple DR detector assemblies (in this example; 3) arranged in a partially overlapping and coplanar way as described above. One of the DR detector assemblies or cassettes is individually marked in the drawing as [104]. The patient is the subject to be imaged, whose radiographic shadow casted from the X-ray source does not fit on one single DR detector, and therefore—in this example—3 DR detector assemblies are used in a single exposure to capture a large area of interest. As is depicted in FIG. 1, multiple DR detector assemblies are arranged in a particular way (the first partially overlapping the next detector assembly at the edge).

Figure 2A:
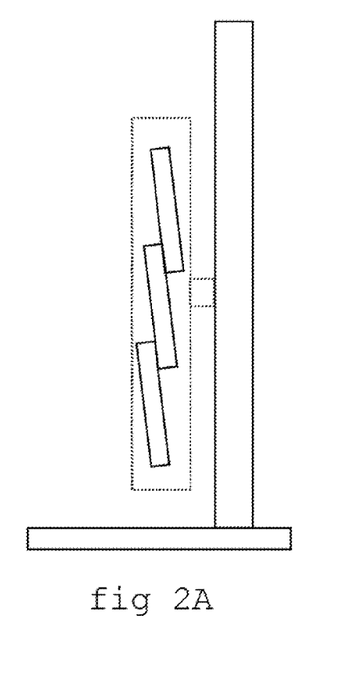
FIG. 2A represents a "coplanar arrangement" of the 3 depicted DR detector assemblies in that the physical centers of said DR detector assemblies are arranged in a coplanar way.
Figure 2B:
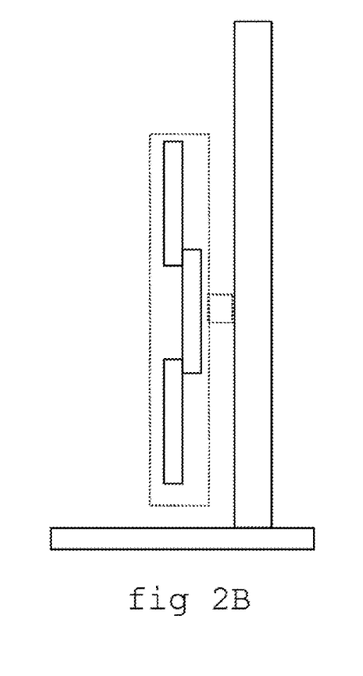
FIG. 2 shows different ways of arranging the DR detector assemblies in a coplanar (2A) or staggered (2B and 2C) way. The DR detector assemblies partially overlap each other in order to form a contiguous detector surface.
Figure 2C:
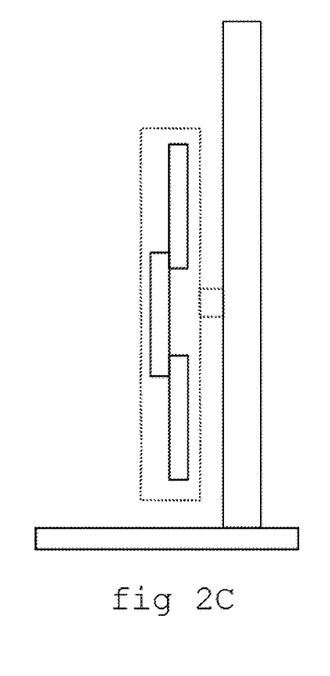

Different ways of arranging the cassettes or DR detector assemblies are conceivable beyond the one depicted in FIG. 1; different other possibilities are depicted in FIG. 2 (A, B and C) in an particular preferred embodiment with 3 DR detectors. Still other arrangements are possible beyond the ones depicted in FIG. 2, for instance for arrangements for 4 or more DR detector assemblies which then can further expand the total imageable surface beyond the surface of a single DR detector assembly.

In this particular preferred embodiment, the individual DR detector assemblies are arranged more or less in one plane and are covering (overlapping) each other's edges partially. The DR detector assemblies are aligned on one axis, providing a contiguous rectangular detector surface. The overlap of the edges of the assemblies may be organized in different ways as depicted in FIG. 2 for an example preferred embodiment of 3 identical DR detector assemblies. 3 different ways of arranging 3 DR detector assemblies are depicted here as an example; other arrangements may be envisaged. In this preferred embodiment, the axis on which the DR detector assemblies are arranged co-planarly is perpendicular to the axis of the incident radiation beam coming from the X-ray source (in order to maintain a constant source-to-detector distance), and the most centrally located DR detector assembly is directly opposed to the X-ray source.

In order to form a contiguous combined rectangular surface, the DR detector assemblies are generally ordered in a "tiled" fashion where the edges are slightly overlapping each other.

These different ways of arrangement of the DR detectors allow for a larger sensor surface compared to what can be achieved by using individual detectors only. The individual DR detector assemblies are typically arranged in their preferred position by an assembly (FIG. 1) supported by a stand (FIG. 1).

The individual DR detector assemblies are preferably ordered in a way that the edges of the neighboring assemblies are partially overlapping with each other in order to obtain in the end a contiguous image without gaps.

As a first step in the process, the group of participating DR detector assemblies in the acquisition of the multi-detector image acquisition needs to be identified. This step is typically a configuration step to be executed by the operator, who selects the DR detector assemblies to be included in the acquisition. This configuration step can be executed by an operator on an acquisition station by making a selection of the representations of the assemblies in a GUI (graphical user interface). The information about the participating assemblies may be sent wirelessly to the assemblies as the list of identification identifiers of the participating assemblies.

Alternatively, in another preferred embodiment, the selection of the participating DR detector assemblies can be performed by setting electronic switches on the DR detector assemblies themselves; the active assemblies would be "switched on" to determine their participation to the acquisition.

Figure 3:
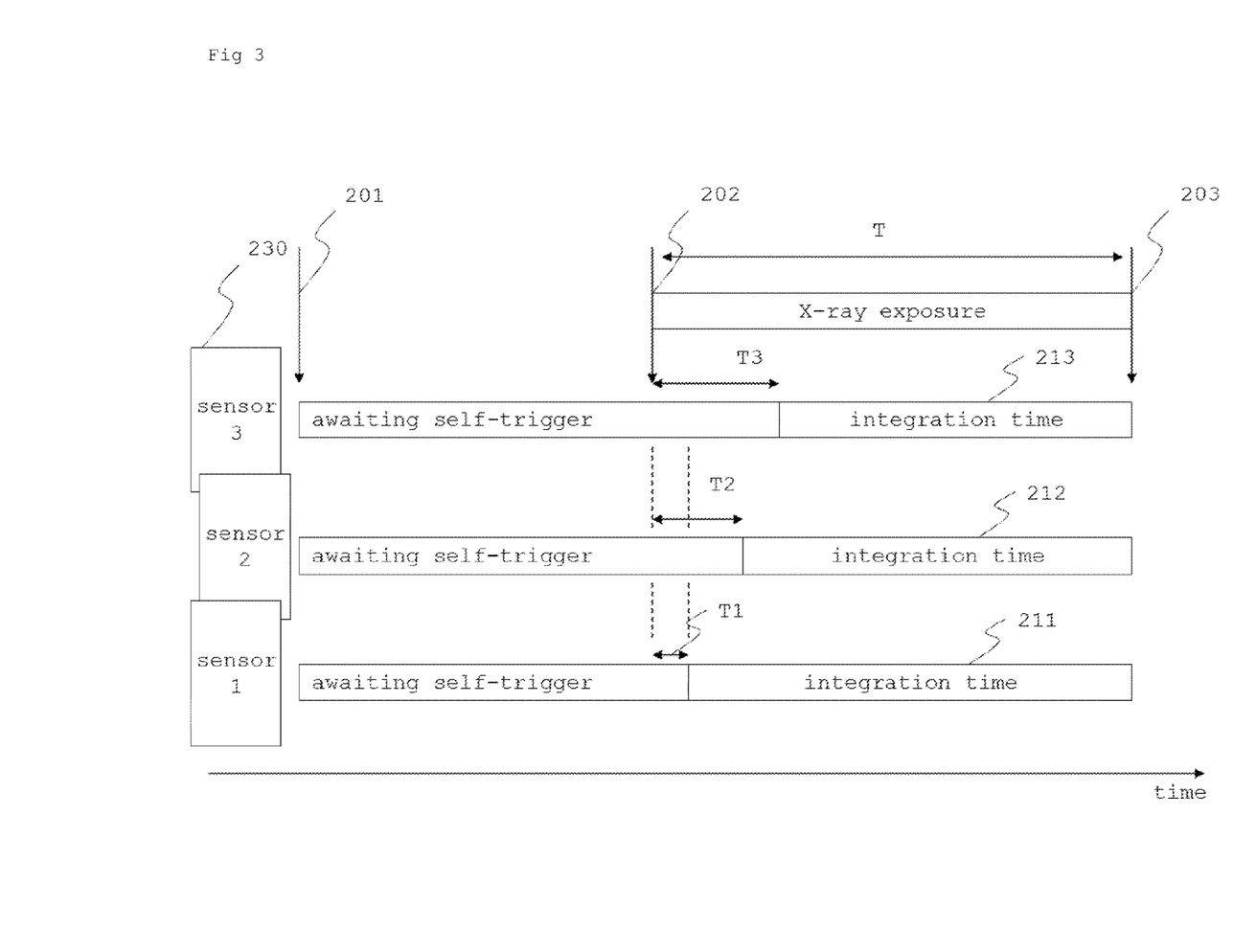
FIG. 3 shows a timeline depicting the different detector events of an example in which 3 identical self-triggering wireless DR detectors would be subject to a single exposure, but would function completely independent from each other. In other words, in the example depicted in this figure the invention is not implemented.

In FIG. 3, the timeline shows the relevant events for a wireless self-triggering setup with multiple DR detectors which are subjected to a single exposure. The multiple DR detectors in this example are functioning independently from each other. FIG. 3 depicts a preferred embodiment of 3 identical self-triggering DR detectors [230], which may at a certain moment in time [201] be signaled by the modality that a new exposure is imminent (the modality will have performed at this point a number of self-checks of its vital subcomponents, like the generator, tube, etc . . . ensuring that the modality is able to perform the exposure). [201] is the moment in time in which the modality will request the individual DR detector assemblies to prepare for exposure, by sending over the exposure details (such as the exposure duration [T], an identification identifier, or other data). These data are sent to the wireless DR detectors by a wireless signal coming from the modality console, modality workstation or X-ray generator.

From that moment on the DR detectors will be awaiting the self-trigger event, which will happen shortly after; the moment in time on which the exposure starts [202] with a duration [T]. [203] is the moment in time representing the end of the exposure, and which thus marks the end of the acquisition period or the integration time. At this moment, the acquisition is complete and the exposure has terminated. After this moment, the image data will be sent from the detector assemblies to the acquisition workstation for processing and storage. [T1] is the time needed for the self-trigger mechanism of the fastest DR detector to respond to kick in after the actual start of the exposure. In the example in FIG. 3, the first DR detector to react to the start of the exposure [202] is "detector 1". [T1] is thus the delay which the self-triggering mechanism of the first DR detector required to sense the start of the exposure. In this period, some of the usable dose for image capture has been used (or, lost for image acquisition). [T2] and [T3] are the equivalent delays for the detectors 2 and 3 respectively, which—as a result of their respective self-triggering mechanisms—are self-triggered. The example in FIG. 3 shows that the periods [T2] and [T3] are longer compared to [T1], and will cause the available integration time [212] and [213] for building up the image to be shorter compared to the integration time available to detector 1 [211].

Since in our example, the integration time for detector 1 equals:

$$Ti(1)=T-T1$$

and, $$T1<T2<T3$$

The following counts:

$$Ti(1)>Ti(2)>Ti(3)$$

Consequently, the integration time for detector 1 is the longest, allowing for the best image acquisition quality of the 3 detector in this example.

In a real application, typical exposure durations vary from a few milliseconds (5 ms-10 ms for a short exposure) till 100 milliseconds (100 ms) or more. The response times for a typical self-trigger mechanism of a wireless DR detector should not exceed 0.5 ms up to 1 ms in order to be effective. Short exposures are particularly sensitive for image quality loss in case of late self-triggering.

Figure 4:
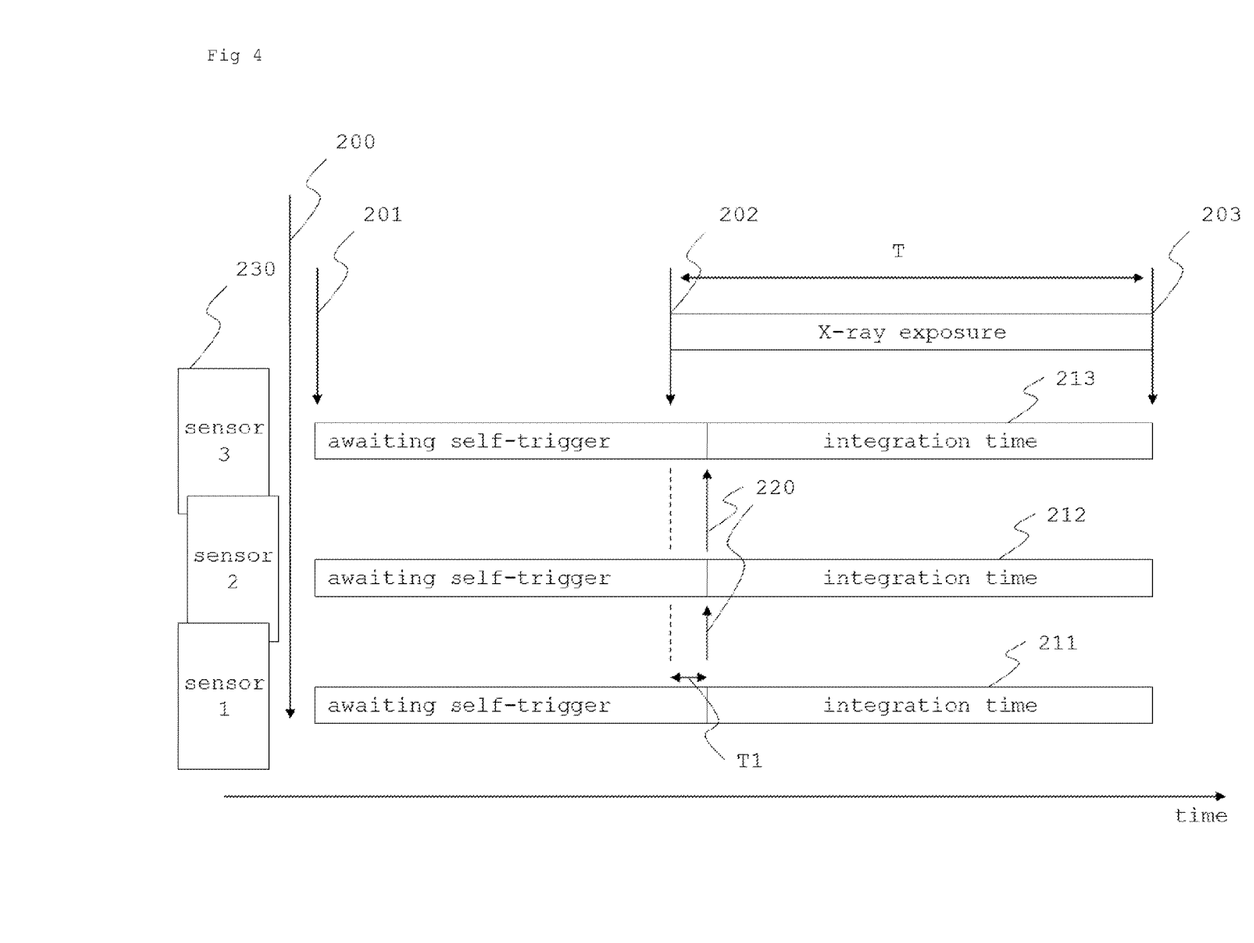
FIG. 4 shows a similar timeline as in FIG. 3, depicting the different detector events of an example in which 3 identical self-triggering wireless DR detectors would be subject to a single exposure, but would function according to the method as described in the invention.

FIG. 4 shows in a same way as FIG. 3 the relevant events for a preferred embodiment of this invention where the multiple identical self-triggering DR detector [230] are subjected to a single exposure. Each of these detector are capable of sending and receiving each other's trigger signals.

The first step in the process is to send an initiation signal [200] (broadcast message) from the modality console, modality workstation or X-ray generator to identify the participating detectors [230]. In a preferred embodiment, the identification of the participating wireless self-triggering DR detectors is done by broadcasting the list of the addresses of all participating DR detectors to all wireless DR detectors. This initiation step [200] is followed by a signal [201] sent from the modality that a new exposure is imminent (the modality will have performed at this point a number of self-checks of its vital subcomponents, like the generator, tube, etc . . . ensuring that the modality is able to perform the exposure). [201] is the moment in time in which the modality will request the participating DR detectors to prepare for exposure, by sending the exposure details (such as the exposure duration [T], an identification identifier, or other data) to all participating DR detectors. These data are sent to the wireless detectors by a wireless signal coming from the modality console, modality workstation or X-ray generator.

From that moment on the DR detectors will be awaiting the self-trigger event [202], which will happen shortly after; it is the moment in time on which the exposure starts [202] with a duration [T]. [T1] is the time needed for the self-trigger mechanism of the most responsive DR detectors to kick in after the actual start of the exposure. In the example in FIG. 5, the first DR detectors to react to the start of the exposure is "detector 1". [T1] is thus the delay which the self-triggering mechanism of the fastest detector requires to sense the start of the exposure. In a preferred embodiment, it is this firstly detected trigger event that will be propagated as trigger [220] for the other participating DR detectors. This method allows that the integration times for all participating DR detectors will become equal to the integration time of the first self-triggered DR detectors to react to the start of the exposure.

$$T_{211}=T_{121}=T_{213}$$

With this concept, there is a gain in integration time for all of the participating self-triggered DR detectors (except for the fastest detector, which keeps the same acquisition time) compared to the situation described in FIG. 3. Since the acquisition time or integration time for the detectors has increased, there will be a positive impact on the image quality across the different DR detectors.

Figure 5:
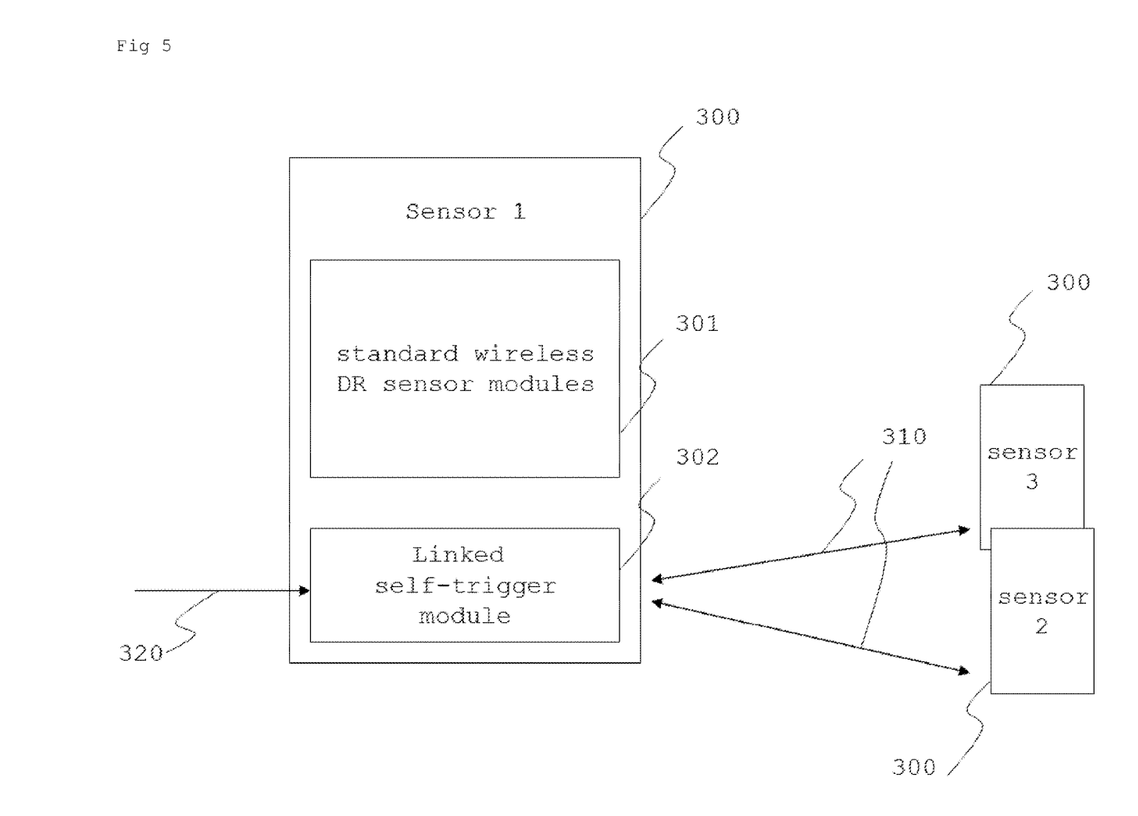
FIG. 5. shows an exploded view of a single self-triggering DR detector assembly [300] which is wirelessly interlinked with 2 other similar DR detector assemblies [330] and [331], wherein a self-triggering DR detector assembly [300] is equipped with all standard wireless self-triggering DR modules [301], but is expanded with a supplementary linked self-trigger module [302]. The standard wireless self-triggering DR detector assembly [301] comprises all other necessary functional elements for a wireless DR detector assembly, including the DR detector component itself, a housing, battery, memory, processor, image read-out- and transfer electronics.

FIG. 5 explains a preferred embodiment of the invention where 3 identical self-triggering DR detectors [300] ([230] in FIGS. 3 and 4) are used, each of these DR detectors are capable of sending and receiving each other's trigger signals, a functionality which is taken care of by the linked self-trigger module [302].

In a preferred embodiment, in a first step, the linked self-trigger module [302] receives the initiation step signal [320] from the modality console. This initiation step signal is a data message over a wireless communication channel [320] containing the relevant data about the upcoming exposure (such as the duration of the exposure and other identification data), and the address data of all participating wireless self-triggering DR detectors in the upcoming exposure. These address data allow that the DR detectors can contact each other, and prevent that other devices would cause interference at the time that the trigger is sent.

In a next step, the linked self-trigger module [302] in the DR detector assembly which detects as a first member of the participating DR detector assemblies the self-trigger event, will send the linked self-trigger signal (or trigger signal) [310] to the other participating and identified DR detectors. These latter DR detectors are able to detect the linked self-trigger signal by the linked self-trigger module [302], and will use the received trigger signal [310] instead of their own self-trigger event. The received trigger event from the first triggered DR detectors will anticipate and replace the "normal" self-trigger event detected by the DR detectors itself.

The linked self-trigger module performs thus three functions; (1) before the exposure, the module receives the exposure data, and the address data of the participating DR detectors. (2) it sends out the self-trigger signal detected by the fastest DR detector of the identified detectors. (3) receive the said linked self-trigger signal from the first participating detector which detects the incoming irradiation in order to start the image acquisition for the detector in question.

The linked self-trigger module may be implemented as a computer program or as a separate self-containing electronic module providing the said functionality. The entire described functionality or parts of it may be implemented as a module or a set of modules on board of the DR detector assembly, but this is not strictly required. The said functionality may be implemented in other components of the DR modality, such as in the DR workstation.

The wireless communication channel referred to in this preferred embodiment may be any well-known wireless communication technique, such as (but not limited to) Wi-Fi, infrared, Bluetooth, radiofrequency, near field or optical communication methods. In a preferred embodiment, the data are sent over a Wi-Fi link.

The invention claimed is:

1. A method for triggering image capture by a group of simultaneously X-ray exposed direct radiography detector assemblies, the method comprising the steps of:
   performing an initiation step to identify a group of participating direct radiography detector assemblies that performs a simultaneous image capture prior to X-ray exposure; and
   detecting the X-ray exposure by a first direct radiography detector assembly of the group of participating direct radiography detector assemblies; wherein
   the first participating direct radiography detector assembly performs a trigger step to signal to all of the group of participating direct radiography detector assemblies to start image capture.

2. The method according to claim 1, wherein the group of participating direct radiography detector assemblies are arranged in a partially overlapping tiled arrangement.

3. The method according to claim 1, wherein the method is used in large field of view radiography applications.

4. The method according to claim 1, wherein the method is used in full-leg full-spine radiography applications.

5. The method according to claim 1, wherein the signal generated by the trigger step is sent wirelessly, optically, electrically, or acoustically.

6. The method according to claim 1, further comprising the step of communicating exposure parameters to the group of participating direct radiography detector assemblies during the initiation step.

7. The method according to claim 1, further comprising the step of alerting the group of participating direct radiography detector assemblies to their participation in a single exposure via a broadcast message.

8. A self-triggering direct radiography detector assembly comprising:
   means for wirelessly receiving identification information of a group of participating direct radiography detector assemblies that perform a simultaneous image capture;
   means for wirelessly sending a trigger signal to start the simultaneous image capture to the group of participating direct radiography detector assemblies;
   means for wirelessly receiving a trigger signal from others of the group of participating direct radiography detector assemblies to start the simultaneous image capture by the direct radiography detector assembly; wherein
   in a case that the direct radiography detector assembly detects a start of an X-ray exposure, the means for wirelessly sending the trigger signal to the group of participating direct radiography detector assemblies is activated; or
   in a case that another of the group of participating direct radiography detector assemblies detects a start of an X-ray exposure, the means for wirelessly receiving the trigger signal initiates image acquisition by the direct radiography detector assembly.

9. The assembly according to claim 8, further comprising:
   means for wirelessly communicating exposure parameters to the group of participating direct radiography detector assemblies when wirelessly receiving the identification information of the group of participating direct radiography detector assemblies.

* * * * *